(12) United States Patent
Junge

(10) Patent No.: US 7,558,630 B2
(45) Date of Patent: Jul. 7, 2009

(54) MEDICAL ELECTRODE DEVICE, PARTICULARLY IMPLANTABLE CARDIOLOGICAL ELECTRODE DEVICE

(75) Inventor: Agur Junge, Berlin (DE)

(73) Assignee: BIOTRONIK CRM Patent AG, Baar (CH)

( * ) Notice: Subject to any disclaimer, the term of this patent is extended or adjusted under 35 U.S.C. 154(b) by 341 days.

(21) Appl. No.: 11/506,917

(22) Filed: Aug. 17, 2006

(65) Prior Publication Data
US 2007/0041781 A1    Feb. 22, 2007

(30) Foreign Application Priority Data
Aug. 18, 2005 (DE) .................. 10 2005 039 039

(51) Int. Cl.
*A61N 1/04* (2006.01)
(52) U.S. Cl. .................. 607/116; 607/115; 607/37
(58) Field of Classification Search .................. 607/116, 607/119, 127, 37
See application file for complete search history.

(56) References Cited

U.S. PATENT DOCUMENTS

| | | | |
|---|---|---|---|
| 2,801,396 A | | 7/1957 | Stegeman |
| 4,387,727 A | * | 6/1983 | Sandstrom .................. 607/116 |
| 4,572,605 A | * | 2/1986 | Hess .................. 439/585 |
| 4,711,027 A | | 12/1987 | Harris |
| 6,038,472 A | * | 3/2000 | Williams et al. .................. 607/5 |
| 6,253,111 B1 | * | 6/2001 | Carner .................. 607/122 |
| 2002/0197905 A1 | | 12/2002 | Kaufmann et al. |

FOREIGN PATENT DOCUMENTS

| | | |
|---|---|---|
| DE | 24 36 889 A1 | 2/1976 |
| DE | 31 50 568 C1 | 2/1983 |
| DE | 32 20 006 C1 | 10/1983 |
| DE | 32 03 300 C2 | 12/1990 |
| DE | 696 05 527 | 4/2000 |
| EP | 0786828 | 7/1997 |
| EP | 786828 A2 * | 7/1997 |

OTHER PUBLICATIONS

German Search Report, dated May 9, 2006.
European Search Report, dated Jun. 12, 2008.

* cited by examiner

*Primary Examiner*—Carl H Layno
*Assistant Examiner*—Jeremiah T Kimball
(74) *Attorney, Agent, or Firm*—Dalina Law Group, P.C.

(57) ABSTRACT

A medical electrode device has a purely mechanical contact connection between electrode and electrical line. For this purpose, a support sleeve is seated in the electrode body, on which the line section to be contacted is wound in a state without its insulation removed. The electrode is placed thereon while enclosing this line section, an internal thread having a cutting zone on the interior of the electrode breaking through the line insulation and being in electrical contact with the electrically conductive core of the electrical line.

5 Claims, 2 Drawing Sheets

MEDICAL ELECTRODE DEVICE, PARTICULARLY IMPLANTABLE CARDIOLOGICAL ELECTRODE DEVICE

This application takes priority from German Patent Application DE 2005 039 039.0 filed Aug. 18, 2005 the specification of which is hereby incorporated herein by reference.

BACKGROUND OF THE INVENTION

1. Field of the Invention

The present invention relates to a medical electrode device and particularly an implantable cardiological electrode device having the features specified in the preamble of claim 1.

2. Description of the Related Art

Electrode devices of this type have been known for some time in form of cardiac electrode catheters, for example, in greatly varying embodiments. They have an oblong, hose-like electrode body made of a medically compatible insulating material and at least one electrode on the electrode body for measuring cardiological stimulation potentials and/or for delivering therapeutically active electrical signals. The present invention relates to electrodes which are rotationally symmetric around the longitudinal axis of the electrode device, i.e., particularly to annular electrodes or also the tip electrodes, which are typically cap-shaped, at the distal end of the electrode body.

An electrical line, which is typically coiled, runs in the electrode body for the electrical connection of the electrode. As is normal, this line has an electrically conductive core and insulation, the core being connected to the electrode to produce an electrical contact.

To produce this electrical contact connection, it is typical to strip the insulation from the core of the lines, which are very filigree because of the dimensions of such electrode devices, with the aid of a scalpel in order to subsequently produce the contact connection with the electrode mechanically or through soldering. Salt abrasion is also practiced to remove the insulation, but is also an extremely complex manufacturing step.

BRIEF SUMMARY OF THE INVENTION

Proceeding from this, the present invention is based on the object of improving a medical electrode device in the area of the electrical contact connection between electrode and line in such a way that a permanently stable, secure contact is ensured easily and particularly without an insulation removal step.

This object is achieved by the features specified in the characterizing part of claim 1. Accordingly, a purely mechanical contact connection is provided between electrode and line, which is constructed on a support sleeve in the electrode body. The line section of the line to be contacted is wound thereon in the state without insulation removed, on which the electrode is seated enclosing this line section. The electrode has a cutting zone on its interior, using which it is in electrical contact with the core of the line while breaking through the insulation.

Therefore, removing insulation from the line may be dispensed with completely to produce the contact. Rather, the insulation is overcome upon application of the electrode to the support sleeve with the line section to be contacted through the action of the cutting zone. Preferably, this may be implemented in an especially elegant construction by providing an internal thread as the cutting zone on the electrode, using which the electrode is screwed onto the line section to be contacted. The screwing on procedure is not only used for the electrical contacting, but rather simultaneously represents the mechanical mounting and fixing of the electrode on the support sleeve with the line lying between them.

According to a further preferred embodiment, the internal thread of the electrode cooperates with an external thread on the support sleeve, so that a cleanly guided, stable, and precisely fitted mounting of the electrode on the support sleeve is achieved while simultaneously producing the electrical contact connection. Furthermore, it is advantageous that if the electrode is reversed briefly against the screwing-on direction, the wire core of the contacting line section displays a clamping or spreading effect, which suppresses further reversal of the electrode and thus removal from the support sleeve. The electrode is thus fixed permanently on the support sleeve.

In a further preferred embodiment, stops are provided on the support sleeve and the electrode as mounting aids, which delimit the screwing-on depth between these two parts. Incorrect mounting is thus effectively prevented.

Further advantageous embodiments particularly relate to electrode devices in which the electrical contacting of the electrodes at the distal end is performed using the coiled multiple line bundles already cited at the beginning. Accordingly, the support sleeve has at least one longitudinal slot, through which a partial bundle, which forms the line section to be contacted and is uncoiled from the multiple line bundle, is guided outward through the support sleeve to be wound onto any exterior. The line guided out may be returned via the same or another longitudinal slot to the remaining multiple line bundle and coiled there again. Preferably, an insulating layer is interposed for further insulation of the individual bundles, which typically contact different electrodes, from one another. The electrical separation between the different poles supplied by the partial bundles of the multiple line bundle is thus improved together with the mechanical seal of the electrode interior to the electrode body in the area of the joins arising through the attached electrode.

BRIEF DESCRIPTION OF THE DRAWINGS

Further features, details, and advantages of the present invention may be inferred from the following description, in which exemplary embodiments of the object of the present invention are explained in greater detail on the basis of the attached drawings.

DETAILED DESCRIPTION

Figures 1, 2:
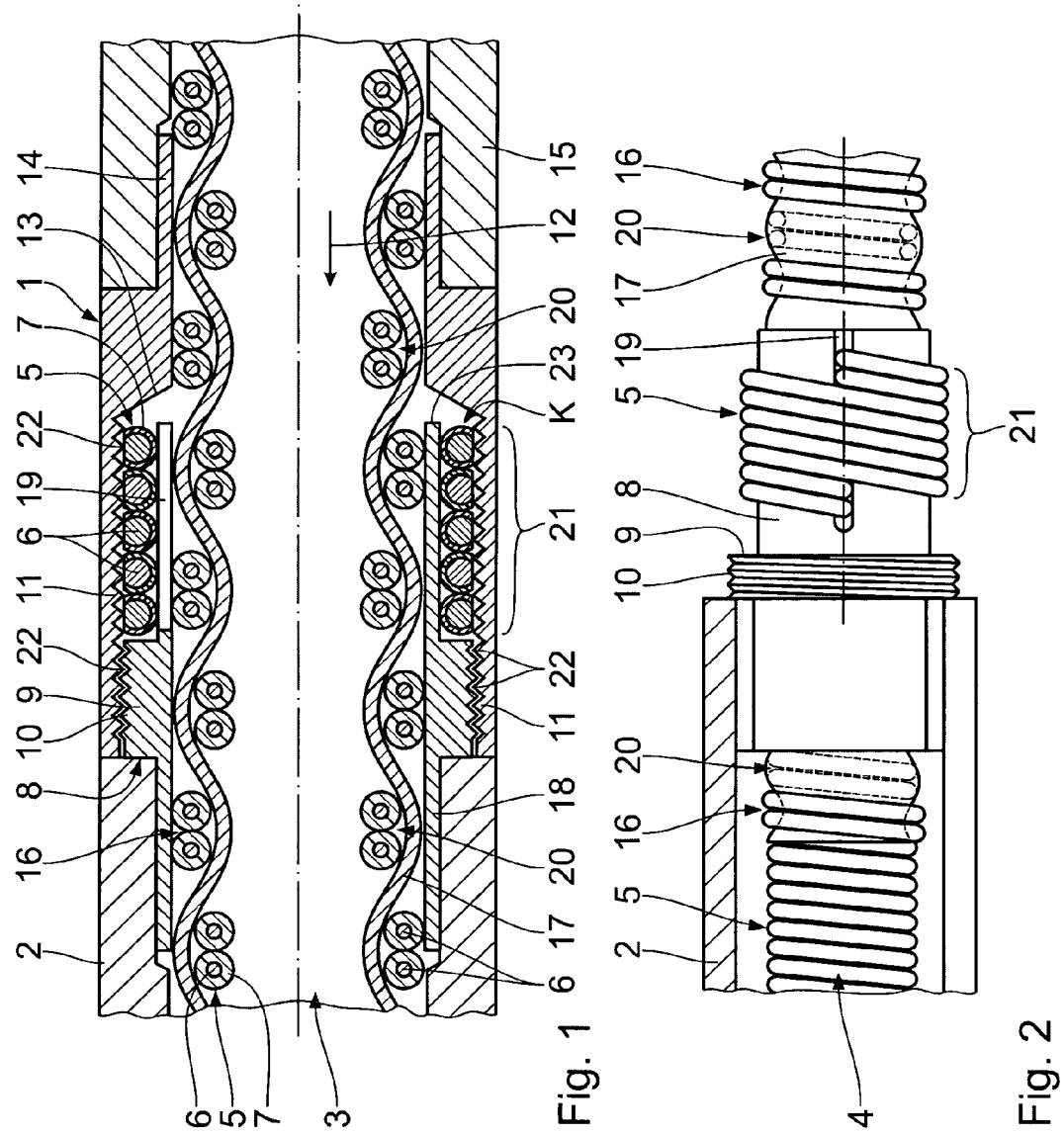
FIG. 1 shows a greatly enlarged, schematic, partial axial section of an electrode device in a first embodiment.
FIG. 2 shows a schematic view of the electrode device, rotated by 90° around the axis of rotation in relation to the section of FIG. 1, in an intermediate manufacturing step.

FIGS. 1 and 2 show details of a cardiac electrode catheter in the area of an annular electrode 1 situated in front of the distal end, which is implemented as isodiametric with the actual oblong, hose-like electrode body 2, made of a silicone material which is compatible with the body.

The electrode body 2 coaxially receives a fourfold coil line bundle 4, which ensures the electrical connection of the annular electrode 1 and a tip electrode (not shown).

Each line 5 of this line bundle 4 has a core 6 having insulation 7 coating it, for example, in the form of a coating made of an insulating lacquer.

As may be seen from FIGS. 1 and 2, a support sleeve 8, which is situated radially inside the annular electrode 1 and the electrode body 2, is used for mounting and contacting the annular electrode 1. This support sleeve 8 has a projecting collar 9 approximately in the middle in relation to its longitudinal extension having an external thread 10 molded onto its exterior, which cooperates with a corresponding internal thread 11 on the interior of the annular electrode 1. The interior thread 11 is significantly longer than the external thread 10 and passes into a stop shoulder 13, which extends radially inward, against the screwing-on direction 12. This reduces the free diameter of the annular electrode 1 to approximately the free internal diameter of the support sleeve 8. Finally, the annular electrode 1 also continues against the screwing-on direction 12 in a plug-on bush 14, whose external diameter is reduced, on which the part 15 of the electrode body 2 running to the distal end of the electrode catheter is plugged and suitably fixed.

To produce the contact connection K between the annular electrode 1 and the line 5, a double partial line bundle 16 is "uncoiled" i.e., removed from the bundle composite, from the coil line bundle 4 starting from a position in front of the annular electrode 1 up to the end (not shown) of the coil line bundle 4. A hose-shaped insulating sleeve 17 is pushed onto the remaining residual line bundle 20 and preferably shrink fitted, after which the double partial line bundle 16 is again wound externally onto the insulating sleeve 17 over a specific length corresponding to the coiling of the remaining line bundle 20 in such a way that the partial line bundle 16 still remains uncoiled for several centimeters in length. Subsequently, the support sleeve 8 is pushed on to the system until the plug-in flange 18 of the support sleeve 8, which runs in the screwing-on direction 12 beyond the collar 9, is pushed into the lumen 3 of the electrode body 2 until the collar 9 stops and is fixed there. Subsequently, the end of the partial line bundle 16 which is not coiled on is guided from the inside to the outside through the axially-parallel longitudinal slot 19 in the support sleeve 8, which is open against the screwing-on direction 12, and wound tightly on the support sleeve 8—as shown in FIGS. 1 and 2. The still remaining length of the partial line bundle 16 is subsequently guided back inward via the longitudinal slot 19 and wound onto the residual line bundle 20 having insulating sleeve 17. The ends are then electrically insulated in a suitable way (not shown) and mechanically protected in the electrode body 15.

Proceeding from this intermediate mounting position shown in FIG. 2, the opening of the annular electrode 1 is pushed onto the line bundle comprising partial line bundle 16 and residual line bundle 20 having insulating sleeve 17 and the support sleeve 8 having the line section 21 to be contacted wound thereon and screwed on with the aid of threads 10, 11. The threads 10, 11 have diameters dimensioned so that the thread webs 22 of the internal thread 11 cut into the insulation 7 of the line 5 when the annular electrode 1 is plugged and screwed on, penetrate this insulation, and produce an electrical contact with the core 6. Therefore, no insulation removal step is required before screwing the annular electrode 1 on in the area of the line section 21 to be contacted. The screwing-on depth of the annular electrode 1 is delimited by the stop shoulder 13 of the annular electrode 1, which cooperates with the front edge 23 of the support sleeve 8 as the counter stop.

After the electrode body 2 is screwed on, the remaining part 15 of the electrode body 2—as described—is pushed onto the line bundle 4 and permanently connected to the annular electrode 2 via the plug-on bush 14.

Figure 3:
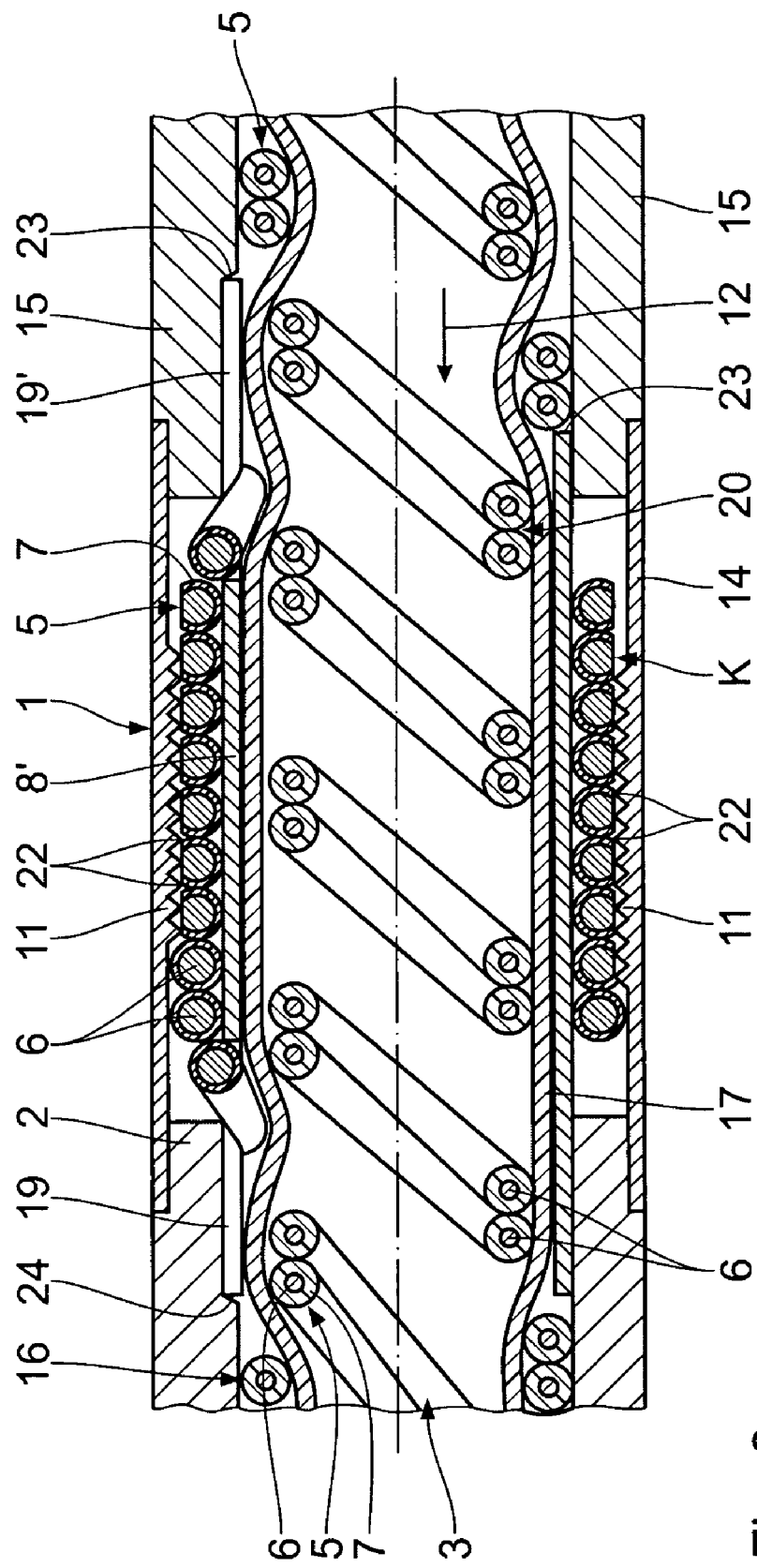
FIG. 3 shows an axial section analogous to FIG. 1 of an electrode device in a second embodiment.

In the exemplary embodiment shown in FIG. 3, the threaded connection is not provided between annular electrode 1 and support sleeve 8'. The latter only has two longitudinal slots 19, 19' open toward the particular front edges 23, 24 facing away from one another, via which the uncoiled partial line bundle 16 is again guided out, wound onto the central part of the support sleeve 8', and subsequently guided back inward again to the residual line bundle 20. The annular electrode 1 is then screwed on to the line section 21 seated externally on the support sleeve 8' using its internal thread 11, the cutting-through effect through the insulation 7 of the line 5 explained above occurring again and an electrical connection being produced between the annular electrode 1 and the core 6 of the line. Otherwise, the construction corresponds to the exemplary embodiment according to FIGS. 1 and 2 and does not need to be explained again.

What is claimed is:

1. An electrode device that is an implantable cardiological electrode device, comprising:

an electrode body (2, 15) that is oblong and hose-like and made of an insulating material;

an electrode (1) that is rotationally-symmetric, and annular wherein said electrode (1) is coupled with said electrode body (2, 15) and wherein said electrode (1) comprises an internal thread (11);

an electrical line (4, 5), which runs through said electrode body (2, 15), having a core (6) comprising at least one electrically conductive core and insulation (7) respectively wrapped individually around each of said at least one electrically conductive core (6);

a support sleeve (8, 8') that is rigid and comprises at least one axially parallel longitude slot (19) that is open on at least one end of said support sleeve (8, 8') and wherein said support sleeve is configured to hold a line section (21);

a cutting zone between said support sleeve (8, 8') and said internal thread (11) wherein said cutting zone is configured to hold said line section (21) between said support sleeve (8, 8') and said internal thread (11) without severing said core (6) of said line section (21) to be contacted of said electrical line (5);

wherein said core (6) is removably connected to said electrode (1) via the internal thread (11) to produce an electrical contact and wherein said electrical contact is a contact connection (K) that is purely mechanical between said electrode (1) and said electrical line (5), wherein removal of said core (6) from said electrode (1) occurs without severing said core (6) and allows said core (6) to be reconnected to said electrode (1) via axial rotation of said electrode (1) with respect to said support sleeve (8, 8') wherein:

said support sleeve (8, 8') in said electrode body (2, 15) on which said line section (21) of said electrical line (5) to be contacted is wound without said insulation removed from said electrical line (5) and on which said electrode (1) is seated while enclosing said line section (21); and, said cutting zone on an interior of said electrode (1) configured to break through said insulation (7) wherein said electrode (1) is in contact electrically with said core (6) of said electrical line (5).

2. The electrode device according to claim 1 wherein an interior of said electrode (1) is configured with an internal thread (11) as said cutting zone that is screwed on to said line section (21) to be contacted.

3. The electrode device according to claim 1 wherein said support sleeve (8) is provided with an external thread (10), which corresponds with said internal thread (11) of said electrode (1) wherein said external thread (10) is configured to screw said electrode (1) together with said support sleeve (8) while simultaneously producing said contact connection (K) between said electrode (1) and said core (6) of said line section (21).

4. The electrode device according to claim 3 wherein said support sleeve (8) and said electrode (1) are provided with stops (13, 23) for delimiting a screw-on depth between said electrode (1) and said support sleeve (8).

5. The electrode device according to claim 1 further comprising an insulating layer (17) interposed between a partial line bundle (16), which is uncoiled from a multiple line bundle (4), and said support sleeve (8, 8') on one side and a residual line bundle (20) on a second side opposing said one side.

\* \* \* \* \*